(12) United States Patent
Yavitz

(10) Patent No.: US 7,494,526 B2
(45) Date of Patent: Feb. 24, 2009

(54) PLANT PROTECTION AND GROWTH STIMULATION BY NANOSCALAR PARTICLE FOLIAL DELIVERY

(76) Inventor: Edward Q. Yavitz, 4105 N. Perryville Rd., Loves Park, IL (US) 61111

( * ) Notice: Subject to any disclaimer, the term of this patent is extended or adjusted under 35 U.S.C. 154(b) by 665 days.

(21) Appl. No.: 11/178,729

(22) Filed: Jul. 11, 2005

(65) Prior Publication Data

US 2006/0014645 A1      Jan. 19, 2006

Related U.S. Application Data

(60) Provisional application No. 60/587,602, filed on Jul. 14, 2004.

(51) Int. Cl.
*A01N 25/34* (2006.01)
(52) U.S. Cl. ............... 71/64.11; 47/57.7; 47/DIG. 10; 71/28; 71/29; 71/30; 71/31; 71/33; 71/48; 71/50; 71/53; 71/64.13; 71/904
(58) Field of Classification Search ............... 71/11–27, 71/28, 29, 30, 31, 33, 53, 48, 50, 904, 64.11, 71/64.13; 47/58.1 R, 58.1 SC, 57.7, DIG. 10
See application file for complete search history.

(56) References Cited

U.S. PATENT DOCUMENTS

| 4,078,052 A | 3/1978 | Papahadjopoulos |
| 5,994,318 A | 11/1999 | Gould-Fogerite et al. |
| 6,592,894 B1 | 7/2003 | Zarif et al. |

FOREIGN PATENT DOCUMENTS

DE          2249552      *   9/1973

OTHER PUBLICATIONS

David Delmarre, PhD; Ruying Lu; Nadine Tatton, PhD; Sara Krause-Elsmore, PhD; Susan Gould-Fogerite, PhD; Raphael J. Mannino, PhD, Title: Formulation of Hydrophobic Drugs Into Cochleate Delivery Vehicles: A Simplified Protocol & Bioral(TM) Formulation Kit (pp. 1-10), date unknown.

* cited by examiner

*Primary Examiner*—Wayne Langel

(57) ABSTRACT

A technique is provided for delivering plant supportive materials to plants. The technique utilizes encapsulation of a plant growth facilitator, such as a plant nutrient, water or pesticide, in small structures that may be taken in through the stomata of plants. This enables a more efficient treatment, watering and/or feeding of plants by foliar application.

19 Claims, 2 Drawing Sheets

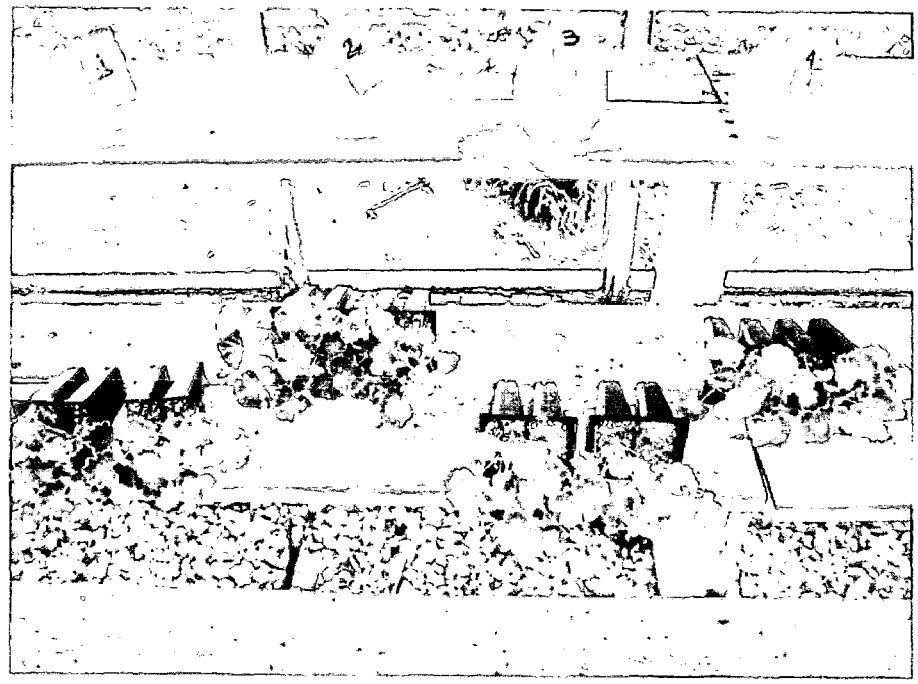
Figure 3     1     2     3     4
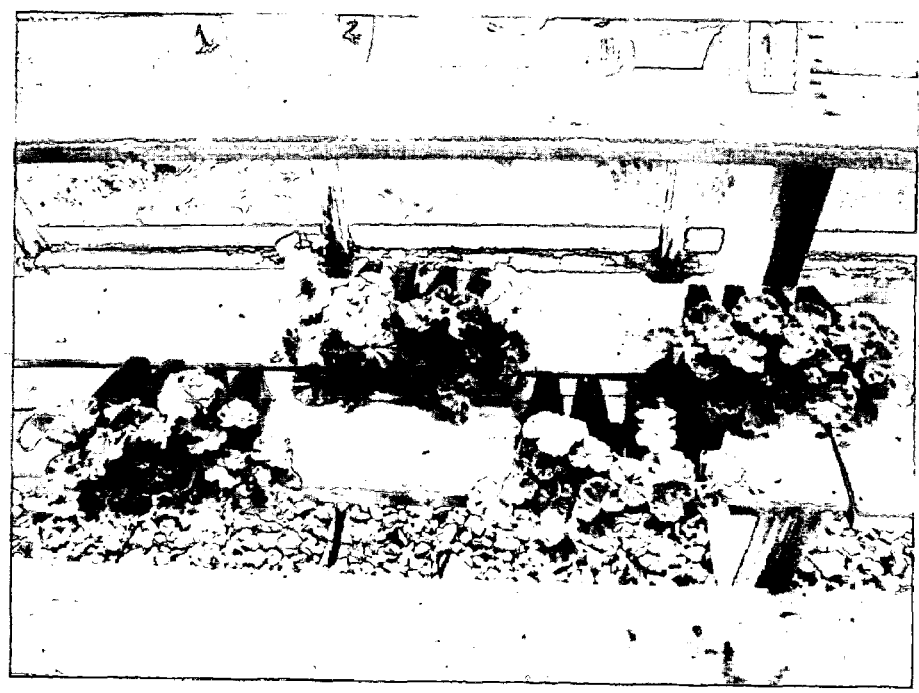
Figure 4     1     2     3     4

PLANT PROTECTION AND GROWTH STIMULATION BY NANOSCALAR PARTICLE FOLIAL DELIVERY

CROSS REFERENCE TO RELATED APPLICATIONS

The following is based on and claims the benefit under 35 USC 119(e) to Provisional Application Ser. No. 60/587,602, filed Jul. 14, 2004

BACKGROUND

For many years, horticulturists and agronomists have subscribed to the belief that foliar feeding of plant nutrients is inefficient and only useful for a specific minor element deficiency as determined by tissue test of plant foliage or leaf petioles.

Dr. H. B. Tukey, plant researcher and Head of Michigan State University's Department of Horticulture in the 1950s, working with research colleague S. H. Wittwer, first proved conclusively that foliar feeding of plant nutrients really works. Researching possible peaceful uses of atomic energy in agriculture, they used radio-active phosphorous and radio-potassium to spray plants, then measured with a Geiger counter, the absorption, movement and utilization of these and many other nutrients within plants. They found plant nutrients surprisingly moved at the rate of about one foot per hour to all parts of the plants. Comparing efficiency of plant use of foliar-fed nutrients versus soil-applied nutrients near roots, they found foliar feeding provided about 95 percent efficiency of use compared to about 10 percent of use from soil applications. See Tukey, H. B. and Wittwer, S. H., 1956. The entry of nutrients into plants through stem, leaf and fruit, as indicated by radioactive isotopes. Progress in Nuclear Energy Biological Sciences Scries Six, pp. 106-114. McGraw-Hill. New York and Permagon Press, London.

Speed of absorption and use by foliar applications proved immediate, whereas with soil applications absorption and plant use both were very slow.

Commercial agricultural chemists began developing foliar feeding formulations a decade ago. Their continuous product improvement research has resulted in products containing not only specific plant nutrients, but also natural plant sugars that aid rapid entry and movement into and through plants, plus cytokinins: natural plant growth hormones extracted from seaweed. Together with nutrients, they aid natural plant defense mechanisms in resisting many plant diseases and insect pests. Healthier plants, like humans, are better able to resist many pests compared to those in stressed, poor condition. Also, growers know and observe that the weakest plants are the ones most often attacked by insect, disease and mite pests. Such products can help improve plants' health for higher yields with lower pest control inputs and plant nutrients costs. A relatively small amount of plant nutrients, foliar-applied, can replace a much greater amount that is soil-applied, and is immediately available to plants.

The development of a low-cost, natural soybean oil-based adjuvant for use with such foliar-applied nutrients and crop protectants further improved leaf and stem coverage and retention. An example is foliar application of (or even to twigs and stems after leaf drop) potassium to benefit berry, grape and tree fruits plants in late fall/early winter, or during winter in milder areas when applied anytime temperatures are above freezing. To toughen/harden plant cells, many farmers apply one gallon per acre of foliar-formulated potassium. In two weeks, a second spray of two gallons of foliar K per acre with 1 pint/acre of the soybean oil is applied. The application adds relatively minimal cost, is rain-fast in 15 minutes and is great insurance at very low cost for high-value horticultural crops. Shortcomings of this type of formulation is that it easily clogs sprayers and drip irrigators and has a short shelf life. Furthermore, it must be applied wet.

SUMMARY

In general, the present invention provides a technique to facilitate the growth of healthy plants. The technique utilizes the folial application of nanoscalar particles that are directly intaken through the stomata of the plants. According to one embodiment, a biologically active material is administered to a plant by encapsulating the biologically active material in a cochleate structure and applying it through foliar application.

BRIEF DESCRIPTION OF THE DRAWINGS

Certain embodiments of the invention will hereafter be described with reference to the accompanying drawings, wherein like reference numerals denote like elements, and:

FIG. 3 is an illustration of plants prior to use in an experiment comparing foliar application of fertilizer encapsulated within cochleates to other applications; and FIG. 4 illustrates the plants of FIG. 3 following the test applications.

DETAILED DESCRIPTION

In the following description, numerous details are set forth to provide an understanding of the present invention. However, it will be understood by those of ordinary skill in the art that the present invention may be practiced without these details and that numerous variations or modifications from the described embodiments may be possible.

The present invention generally relates to plant supportive materials for enhancing plant growth. The plant supportive materials are prepared in stable, dry nanoparticulate formulations of, for example, plant nutrients, encapsulated water, fungicides, insecticides, pest repellents, acaricides and plant growth regulators. The present invention provides such a dry formulation in a nanomolecular structure. Nanoscale materials are materials whose particle diameter in the direction of the largest dimension of the particles is less than 1000 nm (nanometers). In the present specification, the term "nanoparticulate" is used synonymously with the term "nanoscale".

Figure 1:
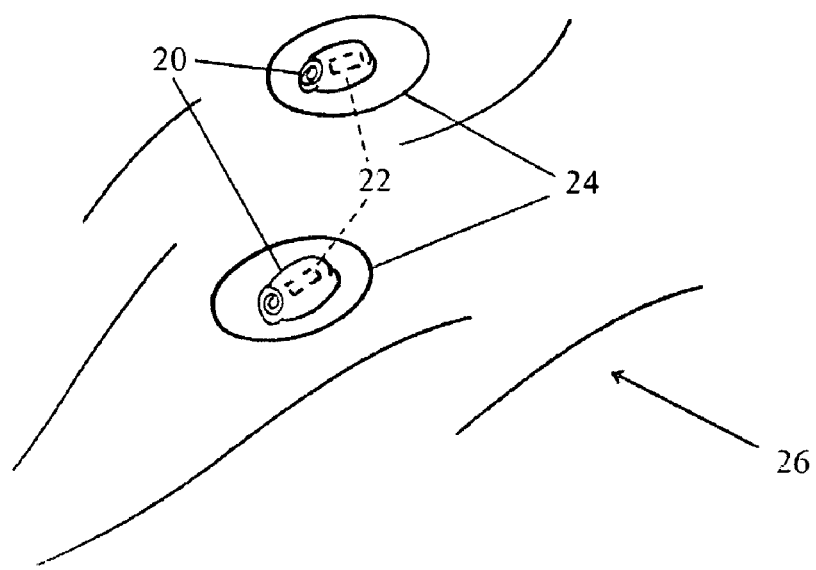
FIG. 1 is a schematic representation of a portion of a plant leaf with stomata through which cochleates pass to provide a plant supportive material directly to cells of a plant, according to an embodiment of the present invention.

The instant invention involves encapsulating plant supportive materials, such as nutrients, water, fungicides, insect repellents, insecticides and their synergists, plant growth regulators and other molecules into a cochleate membrane protein containing a phospholipid vesicle with a large internal space which holds the active ingredients. Because of their nanomolecular size, these loaded cochleates are absorbed into the foliage of plants, as illustrated in FIG. 1. As illustrated, a cochleate 20 contains a plant supportive material 22. The plant supportive material 22 can be directly applied to cells of a plant, because the cochleate 22 can pass through stomata 24, i.e. pores, of plant foliage 26. Accordingly, cochleates 20 can be applied over the leaves of plants for direct delivery of plant supportive material 22 to active cells of the plant where the cochleates fuse with cell membranes inside the leaves to deliver the plant supportive material directly into the cytoplasm of the plant cells, thereby bypassing slower and less efficient uptake methods.

U.S. Pat. No. 5,994,318, which is incorporated herein by reference, teaches the use of cochleates as a means for stabilizing or preserving biologic molecules in a form that is stable at room temperature, capable of desiccation and suitable for oral administration to humans, for delivering polynucleotides to a cell. A formulation comprised of drugs, nutrients and flavors for the stabilization and delivery of the molecules to a cell is disclosed. Oral ingestion of such active ingredients are described applications of these cochleate compositions. However, there is nothing suggesting that nanoparticulate agents can be used with advantage as active principles in foliar feeding of plants.

In the present invention, the anhydrous interior of cochleates preserves active plant protection cargo molecules from ambient conditions while the phospholipid exterior preserves full activity in suspension for extended periods of time.

Cochleate delivery vehicles are stable phospholipid-cation precipitates composed of simple, naturally occurring materials, for example, phosphatidylserine and calcium. They consist of alternating layers of phospholipid and multivalent cations existing as stacked sheets, or continuous, solid, lipid bilayer sheets rolled up in a spiral configuration. In one manufacturing method, the material to be formulated is added to a suspension of liposomes comprised mainly of negatively charged lipids. The addition of multivalent metal ions such as calcium (although other multivalent cations can be used) induces the collapse and fusion of the liposomes into large sheets composed of lipid bilayers, which spontaneously roll up or stack into cochleates. Since the entire cochleate structure is a series of solid layers, components within the interior of the cochleate structure remain intact, even though the outer layers of the cochleate may be exposed to harsh ambient environmental conditions. Cochleate preparations have been shown to be stable for at least one year as a lyophilized powder at room temperature. When the cation rich membrane of a cochleate first comes into approximation to a natural plant membrane, a reordering of the cell membrane is induced, resulting in a fusion event between the outer layer of the cochleate and the cell membrane. This fusion results in the delivery of a small amount of the encochleated material into the cytoplasm of the target cell. The cochleate may slowly fuse or break free of the cell and be available for another fusion event, either with this or another cell. Cochleates may also be taken up by endocytosis, and fuse from within endocytic vesicles.

Examples of materials to be encapsulated in the cochleates include plant nutrients such as water soluble compounds of nitrogen, phosphorus and potassium, alone or in combination, and often in conjunction with other elements such as, for example, calcium, boron, magnesium, zinc, chlorine, etc. Such particular fertilizers can be made of a single component, e.g., urea, ammonium nitrate, potassium chloride, etc., or of multiple components often mixed with inert water soluble or water insoluble materials as in common fertilizers designated as 6-6-6, 4-6-4, 10-10-10, 20-20-5, 14-16-0, 5-20-20, and the like. In addition, specialized cochleate nanostructures may contain water or other optional additives such as herbicides, insecticides, trace elements, iron salts, sulfur and sulfur compounds that produce slow release of nutrients. The cochleate delivery system also can be used to deliver hormones, such as auxin, or proteins, such as TIR1, directly to the cells of plants by foliar application.

Figure 2:
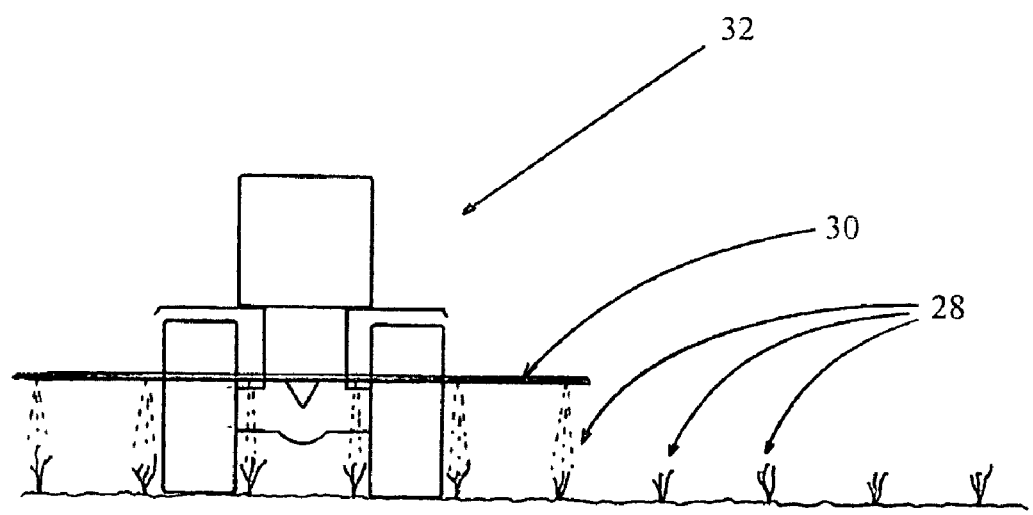
FIG. 2 is a schematic illustration of cochleates containing a plant supportive material being applied to plants, according to an embodiment of the present invention.

The foliar application of cochleates can be conducted according to several methods, such as spraying or dusting the cochleates onto the plants. As illustrated in FIG. 2, for example, the cochleates can be applied to many plants 28 of a given crop planted in a field. In this example, a spreader implement 30 is moved by, for example, a tractor 32 to rapidly apply the encapsulated plant supportive materials to plants 28.

It should be noted that these methods of foliar application can also be used to deliver water directly to plants through their leaves. This method of delivery can greatly conserve water during drought conditions, when planting in dry regions, or in other situations that benefit from water conservation. In this embodiment, cochleates 20 are packed with water and/or other nutrients or plant supportive materials. Because the contents of the cochleate 20 are protected, the encapsulated water will not evaporate even if the cochleates are lypholyzed into a fine dry powder. The powdered cochleates are simply applied to the leaves of a plant to provide water to the plant.

A farmer, for example, can spray or dust the powdered cochleates onto a crop, as illustrated in FIG. 2. The cochleates 20 are taken up by foliar mechanisms through the stomata of the plant leaves whereupon the cochleate phospholipid membranes fuse with the plant cell membranes and release the water and/or other plant supportive materials directly into the cytoplasm of the leaves. Thus, water is conserved until the moment it reaches the plant cell walls rather then undergoing the normal losses of water incurred with conventional or root watering techniques.

In an example, four pairs of commercially grown marigold plants at the same stage of growth were placed on their sides in a greenhouse, as illustrated in FIG. 3. In this example, four spray bottles were filled with the following mixtures, and each spray bottle was paired with a corresponding pair of marigold plants:

1. A commercial plant food (specifically Scott's Miracle-Gro, available from the Scott's company of Marysville, Ohio) containing 15% nitrogen, 30% phosphate, and 15% soluble protein (15-30-15) with trace elements of boron, copper, iron, manganese, zinc and molybdenum was prepared according to instructions at one tablespoon per gallon.
2. Phosphatidylserine (PS) derived from soybean oil (Jarrows formulas, Los Angeles, Calif.) 900 mg was suspended in 300 ml of the 15-30-15 solution of the commercial plant food and water. The mixture was agitated with a glass stirring rod until well mixed to create a liposomal suspension. Cochleate formation was induced through addition of a solution of calcium chloride in a concentration of 10 mM.
3. Phosphatidylserine (PS) derived from soybean oil (Jarrows formulas, Los Angeles, Calif.) 900 mg was suspended in 300 ml of water. Water-filled cochleates were formed through the addition of 10 mM solution of calcium chloride.
4. Water only.

The soil was kept moist by watering every other day. A foliar application of the mixtures was applied by spraying the leaves of each of the four pairs of plants on days 1, 3, 5 and 7. On day 9, the plants had developed, as illustrated in FIG. 4. Specifically, a single flower bud was present in the marigold plants sprayed with only water (bottle 4) and the marigold plants sprayed with water-filled cochleates (bottle 3). One flower bloom appeared on the pair of plants sprayed with the solution of commercial plant food (bottle 1). However, the pair of plants sprayed with the mixture of bottle 2 containing nutrients encapsulated in cochleates had measurably larger foliage, five flower blooms and ten flower buds.

Although only a few embodiments of the present invention have been described in detail above, those of ordinary skill in the art will readily appreciate that many modifications are possible without materially departing from the teachings of this invention. Accordingly, such modifications are intended to be included within the scope of this invention as defined in the claims.

What is claimed is:

1. A method of enhancing plants, comprising:
    administering to a plant a biologically active material encapsulated in a cochleate structure.

2. The method as recited in claim 1, wherein administering comprises spraying the biologically active material encapsulated in the cochleate structure onto multiple plants.

3. The method as recited in claim 1, wherein administering comprises dusting the biologically active material encapsulated in the coclileate structure onto multiple plants.

4. The method as recited in claim 1, wherein administering comprises administering a nutrient in the cochleate structure.

5. The method as recited in claim 1, wherein administering comprises administering a pesticide in the cochleate structure.

6. The method as recited in claim 1, wherein administering comprises administering a hormone in the cochleate structure.

7. The method as recited in claim 1, wherein administering comprises administering a hormone in the form of auxin within the cochleate structure.

8. The method as recited in claim 1, wherein administering comprises administering a protein in the cochleate structure.

9. The method as recited in claim 1, wherein administering comprises administering water within the cochleate structure.

10. A method for treatment or feeding of plants, comprising:
    providing a plant supportive material in cochleates; and
    delivering the cochleates to plant cells by foliar application.

11. The method as recited in claim 10, wherein delivering comprises foliar watering of the plurality of plants with the plant supportive material.

12. The method as recited in claim 10, wherein delivering comprises foliar fertilization of the plurality of plants with the plant supportive material.

13. The method as recited in claim 10, wherein delivering comprises dusting the cochleates onto the plurality of plants.

14. The method as recited in claim 10, wherein delivering comprises spraying the cochleates onto the plurality of plants.

15. The method as recited in claim 10, wherein providing comprises providing water in the cochleate structure.

16. The method as recited in claim 10, wherein providing comprises providing a plant nutrient in the eochleate structure.

17. The method as recited in claim 10, wherein providing comprises providing a plant pesticide in the cochleate structure.

18. A method for treatment or feeding of plants, comprising:
    encapsulating a plant supportive material in particles having diametrical dimensions of less than about 1000 nanometers to facilitate foliar application of the plant supportive material; and
    applying the particles to plants.

19. The method as recited in claim 18, wherein encapsulating comprises encapsulating a plant nutrient.

* * * * *